United States Patent [19]

Mura et al.

[11] Patent Number: 4,746,607
[45] Date of Patent: May 24, 1988

[54] USE OF SUBSTITUTED QUINONE ELECTRON TRANSFER AGENTS IN ANALYTICAL DETERMINATIONS

[75] Inventors: Albert J. Mura; Patricia M. Scensny; Vanessa R. Lum, all of Rochester; Robert T. Belly, Webster, all of N.Y.

[73] Assignee: Eastman Kodak Company, Rochester, N.Y.

[21] Appl. No.: 699,374

[22] Filed: Feb. 7, 1985

[51] Int. Cl.[4] .................. C12Q 1/02; C12Q 1/26; G01N 33/00; G01N 33/50
[52] U.S. Cl. ........................... 435/25; 422/56; 435/29; 435/34; 435/805; 436/93; 436/169; 436/904
[58] Field of Search ............... 422/56, 57, 60; 436/63, 436/93, 120, 169, 170, 172, 518, 904; 435/25, 26, 28, 29, 34, 805; 436/94

[56] References Cited

U.S. PATENT DOCUMENTS

| | | | |
|---|---|---|---|
| 3,415,718 | 12/1968 | Forkman et al. | 195/100 |
| 4,284,704 | 8/1981 | Fleming et al. | 430/154 |
| 4,341,858 | 7/1982 | Chaffee et al. | 430/217 |
| 4,556,636 | 12/1985 | Belly et al. | 435/29 |
| 4,629,696 | 12/1986 | Elstner | 435/25 |

FOREIGN PATENT DOCUMENTS 2740013  3/1979  Fed. Rep. of Germany .

OTHER PUBLICATIONS

E. E. Conn et al. *Outlines of Biochemistry*, 4th Ed., pp. 384 and 385, John Wiley & Sons, Inc., New York, 1976.
H. R. Mahler et al. *Biological Chemistry*, pp. 207 and 594–601, Harper & Row Publishers, Inc., New York, 1966.
Lin et al, *J. Med. Chem.*, 17(5), pp. 558–561 (1974).
Lin et al, *J. Med. Chem.*, 17(7), pp. 668–672 (1974).

*Primary Examiner*—Sidney Marantz
*Assistant Examiner*—David A. Saunders
*Attorney, Agent, or Firm*—J. Lanny Tucker

[57] ABSTRACT

Certain substituted benzo- and naphthoquinone electron transfer agents are useful in analytical compositions, elements and methods, e.g. for determinations of living cells. These electron transfer agents are capable of being reduced by an analyte, and the reduced electron transfer agent, in turn, reduces another compound providing a detectable species (e.g. a dye). The reduction potential (E½) of the electron transfer agents useful in this invention is in the range of from about $-320$ to about $+400$ mV as measured in an aqueous buffer solution at pH 7.

20 Claims, No Drawings

USE OF SUBSTITUTED QUINONE ELECTRON TRANSFER AGENTS IN ANALYTICAL DETERMINATIONS

CROSS-REFERENCE TO RELATED APPLICATIONS

Reference is made to the following commonly assigned application filed on Feb. 7, 1985: U.S. Ser. No. 699,386 by R. T. Belly et al entitled REDUCIBLE COMPOUNDS AND ANALYTICAL COMPOSITIONS, ELEMENTS AND METHODS UTILIZING SAME, which has been abandoned in favor of continuation-in-part U.S. Ser. No. 824,766, filed Jan. 31, 1986.

FIELD OF THE INVENTION

This invention relates to clinical chemistry. In particular, it relates to analytical compositions, elements and methods which utilize certain substituted quinone electron transfer agents to determine analytes (e.g. living cells) in aqueous liquids (e.g. biological fluids).

BACKGROUND OF THE INVENTION

Chemical analysis of liquids, such as water, milk and biological fluids is often desirable or necessary for health maintenance and diagnostic treatment. Various compositions and elements to facilitate such analyses are known. Such compositions and elements generally include a reagent composition for determining a substance under analysis, termed an analyte herein. The analyte can be a biological organism or a nonliving chemical substance. This reagent composition, upon interaction with the analyte, provides a detectable change (e.g. dye formation).

Recently, much work has been directed to developing compositions and elements which are useful for rapid and highly quantitative diagnostic or clinical analysis of biological fluids such as whole blood, serum, plasma, urine and the like.

For the rapid and effective diagnosis and treatment of infectious diseases, it is desirable to be able to detect the bacteria causing the disease as rapidly as possible. Infections of the urinary tract are among the most common bacterial diseases, second in frequency only to infections of the respiratory tract. In fact, in many hospitals, urinary tract infections are the most common form of nosocomial infections, often following the use of catheters and various surgical procedures. Most urinary tract infections (UTI) result from ascending infection by microorganisms introduced through the urethra and vary in severity from an unsuspected infection to a condition of severe systemic disease. Such infections are usually associated with bacterial counts of 100,000 ($10^5$) or more organisms per ml of urine, a condition referred to as significant bacteriuria. Under normal conditions, urine is sterile, although contamination from the external genitalia may contribute up to 1,000 ($10^3$) organisms per ml in properly collected and transported specimens.

Significant bacteriuria may be present in a number of pathological conditions involving microbial invasion of any of the tissues of the urinary tract, or may result from simple bacterial multiplication in the urine without tissue invasion. The infection may involve a single site such as the urethra, prostate, bladder, or kidney, although frequently it involves more than one site. Infection restricted to the urine may present itself as asymptomatic bacteriuria, i.e., a condition which manifests no overt signs or symptoms of infection. Early treatment of this condition can prevent the development of more serious conditions, e.g., pyelonephritis (inflammation of the kidney and the renal pelvis). The rapid detection of bacteria by a reliable method would therefore facilitate an early and specific diagnosis.

Further, in order to insure that a prescribed antibiotic is in fact effective in treating an infection, repeated tests during therapy are required. The need for simple, rapid bacteriuria tests is thus clear. Moreover, in view of the frequent unsuspected asymptomatic occurrences of UTI among children, pregnant women, diabetics and geriatric populations, diagnosis of which may require collection and testing of several specimens, bacteriuria tests must be sufficiently simple and economical to permit routine performance. Again, this illustrates the need for a rapid and inexpensive bacteriuria detection method.

Known commercial methods for relatively rapid detection of bacteria or other living cells have a number of serious drawbacks. It was during attempts to find solutions to these problems that our colleagues unexpectedly discovered that certain reducible compounds would provide detectable dyes to enable rapid detection of bacteria or other analytes at pH 9 or less. This discovery is the subject of U.S. Ser. No. 699,386 of Belly et al, noted above. As described in that patent application, determination of certain analytes, notably living cells (such as bacteria, yeast, etc.), is best accomplished using a reducible compound which releases a shiftable detectable species to provide a detectable species in the presence of an electron transfer agent (ETA). The electron transfer agent is first reduced by the living cell. The reduced ETA then reduces the reducible compound whereupon the shiftable detectable species is released. Phenazine methosulfate (PMS) is the preferred ETA used by Belly et al in the practice of their invention.

While the Belly et al invention represents a significant advance in the art, PMS and structurally related ETAs are unstable in aqueous solutions. This instability leads to premature release of the shiftable detectable species. This undesirable release is evidenced by high background levels which must be subtracted from assay results to accurately determine the analyte. The background may significantly affect the results when low level analytes (e.g. low levels of bacteria) are being measured.

Other known ETAs which have been tried in biological studies, e.g. pyrocyanine and menadione, are generally ineffective in promoting release of a shiftable detectable species.

Hence, there is a need in the art for a rapid and highly quantitative assay for analytes in aqueous liquids that is not subject to high background levels.

SUMMARY OF THE INVENTION

The present invention provides a means for the determination of analytes, e.g. microorganisms, which avoids the problems encountered with known assays. In particular, this invention avoids the problem of premature release of detectable species (e.g. dye) associated with the ETAs taught in the art. The present invention also provides a means for obtaining more rapid and highly sensitive assays, particularly of microorganisms.

The analytical compositions, element and method of this invention provide the unexpected properties described herein because they utilize an ETA chosen from a certain class of substituted quinones.

Therefore, in accordance with this invention, a composition for determination of an analyte in a liquid comprises:

(a) an at least partially substituted benzo- or naphthoquinone electron transfer agent (ETA) which is capable of being reduced by the analyte and has an $E_{\frac{1}{2}}$ of from about $-320$ to about $+400$ mV as measured in an aqueous buffer solution at pH 7, (b) a reducible compound which provides a detectable species when reduced by the reduced ETA, and, (c) a buffer which maintains the composition pH at 9 or less.

This invention also provides a dry analytical element for determination of an analyte in a liquid. This element comprises an absorbent carrier material, the ETA described above, and a reducible compound which provides a detectable species when reduced by the reduced ETA.

Further, this invention provides a method for the determination of an analyte in a liquid. This method comprises the steps of:

A. at a pH of 9 or less, physically contacting a sample of the liquid with the benzo- or naphthoquinone electron transfer agent (ETA) described above, and a reducible compound which provides a detectable species upon reduction by the reduced ETA, and B. detecting the detectable species.

DETAILED DESCRIPTION OF THE INVENTION

As noted above, the advantages obtained with the present invention are achieved due to the use of particular electron transfer agents (ETAs) in the practice of this invention. These ETAs are highly compatible with both aqueous and oleophilic environments. They have sufficient hydrophilic character to be soluble in aqueous buffer solutions. At the same time, they have sufficient oleophilic character to allow interaction with electron donor within the cells.

In general, the ETA useful in this invention is an at least partially substituted benzo- or naphthoquinone which can be represented by either of the following structures (Ia and b):

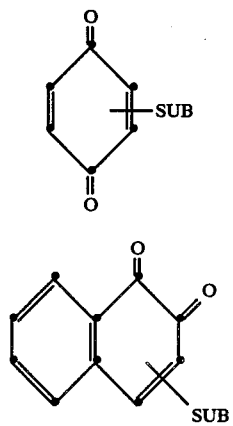

wherein SUB represents one or more substituents which give the compound its desirable reduction potential ($E_{\frac{1}{2}}$) within the range of from about $-320$ to about $+400$ mV as measured in buffer at pH 7 using standard techniques described below in more detail.

SUB can be one or more electron withdrawing or electron releasing groups as they are commonly known in the art as long as the combination of groups provides the compound with the desired $E_{\frac{1}{2}}$ value. Representative electron withdrawing groups include chloro, bromo, fluoro, acetyl, and others known in the art. Representative electron releasing groups include methyl, methoxy, hydroxymethyl, ethoxy, and others known in the art. Alternatively, the SUB substituents on the structure (Ia) above can be combined to provide an aromatic or nonaromatic carbocyclic or heterocyclic ring fused with the quinone nucleus. The fused ring can also contain suitable substituents which would be known to one of ordinary skill in the art.

Particularly useful ETAs are those having the structure (II):

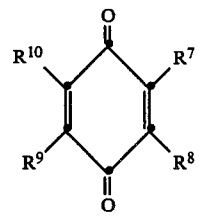

In this structure, $R^7$ and $R^8$ are independently hydrogen, substituted or unsubstituted alkyl or alkenyl (generally of 1 to 10 carbon atoms, e.g. methyl, ethyl, chloromethyl, 2-propenyl, n-hexyl, decyl, etc. and preferably of 1 to 5 carbon atoms), substituted or unsubstituted alkoxy (defined similarly to alkyl), substitued or unsubstituted hydroxyalkyl (generally of 1 to 10 carbon atoms, e.g. hydroxymethyl, hydroxyethyl, 2-hydroxypropyl, 2-hydroxyisopropyl, etc. wherein the alkyl portion can be further substituted and preferably of 1 to 5 carbon atoms), substituted or unsubstituted hydroxyalkoxy (defined similarly to hydroxyalkyl), substituted or unsubstituted acetoxyalkyl (generally of 1 to 10 carbon atoms in the alkyl portion of the molecule which can be defined as for alkyl above, e.g. acetoxymethyl, acetoxyethyl, etc. and preferably of 1 to 5 carbon atoms), substituted or unsubstituted acetoxyalkoxy (generally of 1 to 10 carbon atoms in the alkoxy portion of the molecule and defined similarly to acetoxyalkyl above, and preferably of 1 to 5 carbon atoms), substituted or unsubstituted alkoxyalkyl or alkoxyalkoxy (each generally having 2 to 10 carbon atoms with the alkoxy and alkyl portions of the molecule defined similarly to alkly and alkoxy above), substituted or unsubstituted aryl (generally of 6 to 12 carbon atoms, e.g. phenyl, naphthyl, xylyl, methylnaphthyl, p-methoxyphenyl, etc.), substituted or unsubstituted alkaryl (generally of 7 to 10 carbon atoms, with the alkyl and aryl portions of the molecule defined similarly to alkyl and aryl above, e.g. benzyl, phenylethyl, p-methoxyphenylethyl, etc.), heterocycle or alkylheterocyclic groups (generally of 5 to 12 carbon, nitrogen, oxygen or sulfur atoms in the ring, with one or more substituents if desired, e.g. morpholino, piperidino, methylpiperidino, etc.). Preferably, $R^7$ and $R^8$ are independently hydrogen, alkyl, alkoxy, or hydroxyalkyl as defined above.

Also, in structure II above, $R^9$ and $R^{10}$ are independently $R^7$ and $R^8$, or taken together, supply the carbon, nitrogen, oxygen or sulfur atoms to complete a 4- to 8-membered fused substituted or unsubstituted carbocyclic or heterocyclic ring attached to the quinone nucleus (e.g. to complete a cyclopentane, dihydrofuran, or bicyclic ring, such as bicyclo[2.2.2]octane, benzo, or a bicyclo[2.2.1]heptane ring). Preferably, $R^9$ and $R^{10}$ are independently one of the groups defined for $R^7$ and $R^8$, or taken together, supply the carbon atoms to complete a 6- to 8-membered fused carbocyclic ring.

At least one of the substituents, $R^7$, $R^8$, $R^9$ and $R^{10}$, is not hydrogen, but is one of the groups defined above, or is taken with another substitutent to form the defined fused ring.

It is essential that the ETAs useful in the practice of this invention have a reduction potential ($E_{\frac{1}{2}}$) within the range of from about $-320$ to about $+400$ mV when measured in an aqueous buffer solution at pH 7. Preferably, The $E_{\frac{1}{2}}$ of the ETA is in the range of from about $-185$ to about $+400$ mV. The desired $E_{\frac{1}{2}}$ is achieved by having the appropriate substituents on the quinone nucleus of the compound. With the teaching provided herein, a person skilled in synthetic chemistry would know what substituents to put on the quinone nucleus to obtain the desired $E_{\frac{1}{2}}$. Reduction potential measurements can be made according to conventional electrochemical techniques using either differential pulse polarography or cyclic voltametry (see, e.g. Sawyer and Roberts, Jr., *Experimental Electrochemistry for Chemists*, John Wiley & Sons, New York, 1974).

Representative ETAs useful in this invention are listed in Table I below in reference to structure II shown above.

TABLE I

| ETA Compound | $R^7$ | $R^8$ | $R^9$ | $R^{10}$ |
|---|---|---|---|---|
| I | $-CH_2OH$ | $-H$ | $-CH_3$ | $-CH_3$ |
| II | $-OCH_3$ | $-H$ | $-OCH_3$ | $-H$ |
| III | $-CH_3$ | $-H$ | $-CH_3$ | $-CH_3$ |
| IV | $-OCH_3$ | $-OCH_3$ | $-H$ | $-CH_3$ |
| V | $-OCH_3$ | $-H$ | $-H$ | $-OCH_3$ |
| VI | $-OCH_3$ | $-OCH_3$ | $-OCH_3$ | $-OCH_3$ |
| VII | $-OCH_2CH_3$ | $-H$ | $-OCH_2CH_3$ | $-H$ |
| VIII | $-CH_3$ | $-CH_3$ | $-CH_3$ | $-CH_3$ |
| IX | $-CH_3$ | $-CH_3$ | $-H$ | $-H$ |
| X | $-O(CH_2)_2OCH_3$ | $-H$ | $-O(CH_2)_2OCH_3$ | $-H$ |
| XI | $-OCH_3$ | $-OCH_3$ | $-OCH_3$ | $-CH_3$ |
| XII | $-CH(OH)CH_3$ | $-H$ | $-CH_3$ | $-H$ |
| XIII | $-OCH_3$ | $-OCH_3$ | $-H$ | $-H$ |
| XIV | $-CH(OCH_3)CH_3$ | $-H$ | $-CH_3$ | $-H$ |
| XV | $-CH(OH)CH_2CH_3$ | $-H$ | $-CH_3$ | $-H$ |
| XVI | $-CH(OC(O)CH_3)CH_3$ | $-H$ | $-CH_3$ | $-CH_3$ |
| XVII | $-CH_3$ | $-H$ | $R^9$ and $R^{10}$ together form | |
| XVIII | $-OCH_3$ | $-H$ | $R^9$ and $R^{10}$ together form | |
| XIX | $-OCH_3$ | $-H$ | $R^9$ and $R^{10}$ together form | |
| XX | $-OCH_3$ | $-H$ | $R^9$ and $R^{10}$ together form | |
| XXI | $-CH_3$ | $-H$ | $R^9$ and $R^{10}$ together form | |

TABLE I-continued

| ETA Compound | R⁷ | R⁸ | R⁹ | R¹⁰ |
|---|---|---|---|---|
| XXII | —CH₂CH₂OH | —H | —OCH₃ | —H |
| XXIII | —OCH₃ | —OCH₃ | R⁹ and R¹⁰ together form | |
| XXIV | —OCH₃ | —H | R⁹ and R¹⁰ together form | |
| XXV | —CH₃ | —H | R⁹ and R¹⁰ together form | |
| XXVI | —CH₂CH₂OH | —H | R⁹ and R¹⁰ together form | |
| XXVII | —CH₂OH | —H | R⁹ and R¹⁰ together form | |
| XXVIII | —CH₃ | —CH₃ | R⁹ and R¹⁰ together form | |
| XXIX | —CH₂OH | —CH₃ | R⁹ and R¹⁰ together form | |

ETAs I, III, IV, XXVI and XXVII of Table I are particularly useful in the practice of this invention, with ETAs I, III and IV (2,3-dimethyl-5-hydroxymethyl-1,4-benzoquinone and 2,3,5-trimethyl-1,4-benzoquinone and 2,3-dimethoxy-5-methyl-1,4-benzoquinone, respectively) being most preferred.

Another useful ETA having the structure (Ib) above is

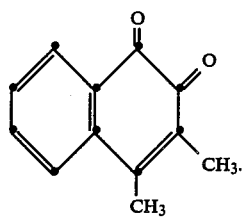

Other substituted quinones which can be used in the practice of this invention, provided they have the desired properties, are described in U.S. Pat. No. 4,284,704 (issued Aug. 18, 1981 to Fleming et al), the disclosure of which is incorporated herein by reference as it relates to quinone compounds.

The ETAs described herein can be prepared using starting materials and procedures known in the art to a skilled synthetic chemist. Generally, the ETAs are prepared according to the following sequence of reactions: (1) protection of the hydroquinone groups, (2) attachment of the appropriate substituents to the protected hydroquinone nucleus, (3) removal of the protecting groups, and (4) conversion of the hydroquinone to a quinone. Representative preparations of some ETAs are provided in the illustrative preparations preceding the Examples below.

The ETAs described herein are used in combination with a reducible compound which can provide a detectable species when reduced by the ETA. The detectable species can be obtained by the reducible compound undergoing a change to become detectable.

Alternatively, the detectable species can be obtained by release from the reducible compound. The detectable species can be a material which is directly detectable by a suitable means, as well as a material which can react with other substances, e.g. other analytes, enzymes, mordants, metal ions or other materials to provide a detectable species. Such species includes those detectable by radiometric means, including chromogens (e.g. dyes or pigments) which can be detected colorimetrically, and fluorogens (e.g. fluorescent dyes or probes) which can be detected fluorometrically. Additionally, the detectable species can be a phosphorescent species, a radioactively tagged species, or a chemiluminescent species, or any other detectable species known to one skilled in the art.

Useful reducible materials include tetrazolium salts which can be reduced to form colorimetric dyes, dichloroindophenol dyes which can be reduced to colorless compounds, and other dye-providing materials which can be reduced.

Particularly useful reducible compounds are those described and claimed by Belly et al in U.S. Ser. No. 699,386 noted above, the disclosure of which is incorporated herein by reference. The reducible compounds of that application provide significant advantages in analytical determinations because of their very rapid release of a detectable species at physiological pH (i.e. pH of 9 or less).

While the details of such reducible compounds can be obtained from the patent application noted above, generally such compounds are represented by the structure CAR—(R$^1$)$_n$ wherein CAR— is an aromatic or quinone nucleus, R$^1$ is a moiety which comprises a shiftable detectable species, and n is 1 or 2, provided that the reducible compound is capable of being reduced at a pH of 9 or less to release the shiftable detectable species, and further provided that when R$^1$ is replaced with H, CAR—(H)$_n$ has an E$_{\frac{1}{2}}$ of either at least about +100 mV when measured in water, or of at least about −650 mV when measured in acetonitrile.

Preferably, the reducible compounds used in the practice of this invention are those of the novel class of reducible intramolecular nucleophilic displacement, or RIND, compounds described in detail in the noted Belly et al application. Such RIND compounds are represented by the structure

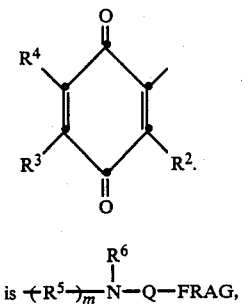

$$R^1 \text{ is } -(R^5)_m-\underset{\underset{R^6}{|}}{N}-Q-FRAG,$$

wherein m is 0 or 1, and preferably 1. R$^5$ is substituted or unsubstituted alkylene, preferably of 1 or 2 carbon atoms in the backbone (e.g. methylene, ethylene, alkoxymethylene, etc.). Most preferably, R$^5$ is methylene. Q is carbonyl or thiocarbonyl and preferably carbonyl.

R$^6$ is substituted or unsubstituted alkyl preferably of 1 to 40 carbon atoms (e.g. methyl, ethyl, n-propyl, isopropyl, t-butyl, hexyl, decyl, lauryl, benzyl, etc.), substituted or unsubstituted cycloalkyl preferably of 4 to 40 carbon atoms (e.g. cyclobutyl, cyclohexyl, 4-methylcyclohexyl, etc.), or substituted or unsubstituted aryl of 6 to 40 carbon atoms (e.g. phenyl, xylyl, naphthyl, p-nitrophenyl, anthryl, p-t-butoxyphenyl, etc.). Preferably, R$^6$ is lower alkyl of 1 to 6 carbon atoms (substituted or unsubstituted) or phenyl (substituted or unsubstituted), and more preferably, R$^6$ is lower alkyl of 1 to 3 carbon atoms (e.g. methyl, ethyl, isopropyl, etc.).

FRAG is a shiftable detectable species which, when cleaved from the RIND compound, provides a detectable species. This species is released in an amount which can be directly related to the amount of reductant present. The specific composition of FRAG can vary considerably depending upon the type of detectable species desired and upon the particular detection means employed.

The detectable species can be a material which is directly detectable by a suitable means, as well as a material which can react with other substances, e.g. other analytes, enzymes or other reagents to provide a detectable species. Such species include chromogens (e.g. dyes or pigments) which can be detected colorimetrically and fluorogens (e.g. fluorescent dyes or probes) which can be detected fluorometrically. Additionally, the detectable speies can be a phosphorescent species, or a chemiluminescent species, or any other detectable species known to one skilled in the art.

Particularly useful shiftable detectable moieties are chromogens and fluorogens having a first spectral absorption band prior to release and a second spectral absorption band when measured after release. Examples of useful classes of chromogens are azo, azomethine, nitrophenol, indophenol, indoaniline and triarylmethane dyes, and others known in the art, with azo dyes being preferred. Examples of useful classes of fluorogens are coumarin, fluorescin and rhodamine fluorescent dyes, and others known in the art.

Useful phosphorescent species include such phosphors as 2',5'-dibromofluorescein and 4',5'-diiodofluorescein. A useful chemiluminescent species is luciferin.

FRAG generally is linked to Q by means of a single bond or a bivalent monoatom linkage which is a part of FRAG. Preferably, the monoatom linkage is an element of the VIA group of the Periodic Table in its −2 valence stage, e.g. oxygen, sulfur, selenium, etc.

$R^2$, $R^3$ and $R^4$ in the above quinone structure are independently hydrogen, substituted or unsubstituted alkyl of 1 to 40 carbon atoms (e.g. methyl, ethyl, hydroxymethyl, methoxymethyl, etc.) substituted or unsubstituted aryl (e.g. phenyl, naphthyl, methylnaphthyl, p-nitrophenyl, m-methoxyphenyl, phenylsulfonamido, etc.) or an electron withdrawing group which generally has a positive Hammett sigma value, and preferably has a sigma value greater than about 0.06. Hammett sigma values are calculated in accordance with the procedures described in *Steric Effects in Organic Chemistry*, John Wiley & Sons, Inc., 1956, pp. 570–574 and *Progress in Physical Organic Chemistry*, Vol. 2, Interscience Publishers, 1964, pp. 333–339. Typical useful electron withdrawing groups having positive Hammett sigma values include cyano, carboxy, nitro, halo (e.g. fluoro, bromo, chloro, iodo), trihalomethyl (e.g. trifluoromethyl, trichloromethyl, etc.), trialkylammonium, carbonyl, carbamoyl, sulfonyl, sulfamoyl, esters and others known in the art, or alkyl or aryl groups (defined above) substituted with one or more of these electron withdrawing groups. Preferred electron withdrawing groups include nitro, cyano, p-nitrophenyl, p-cyanophenyl and 2,5-dichlorophenyl. Aryl groups with methoxy or acetamido groups in the meta position are also useful.

$R^3$ can also be $R^1$ thereby potentially providing a 2:1 molar ratio of detectable species to RIND compound.

Alternatively, $R^3$ and $R^4$, taken together, can represent the carbon atoms necessary to complete a substituted or unsubstituted fused carbocyclic ring attached to the quinone nucleus. For example, such a ring (mono- or bicyclic) can have from 4 to 8, and preferably from 5 to 7, carbon atoms in the backbone.

It is essential that when $R^1$ of CAR–$(R^1)_n$ is replaced by a hydrogen atom, CAR–$(H)_n$ has an $E_{\frac{1}{2}}$ of either at least about $+100$ mV when measured in water, or of at least about $-650$ mV when measured in acetonitrile. Such measurements are made according to conventional electrochemical techniques using either differential pulse polarography or cyclic voltametry (see, e.g. Sawyer & Roberts, Jr., reference, noted above). Preferably, the $E_{\frac{1}{2}}$ is from about $+100$ to about $+400$ mV as measured in water or from about $-650$ to about $-300$ mV as measured in acetonitrile. The desired $E_{\frac{1}{2}}$ is achieved by having appropriate electron withdrawing groups on the CAR—nucleus, or by a combination of a fused ring attached to the nucleus and electron withdrawing groups.

For the RIND compounds described above, it is further preferred that when the compound is reduced at about pH 7, at least about 50% of the FRAG moiety is released within about 30 minutes.

In the practice of the invention, RIND compounds V, VII, VIII, IX, XX and XXIV of Table I of the Belly et al application are preferred.

The ETA and reducible compound can be combined with a buffer solution to provide a composition. Useful buffers include those which will maintain the pH of the composition at 9 or less, and preferably from about 6.5 to about 8. Representative buffers include phosphates, borates, N-2-hydroxyethylpiperazine-N'-2-ethane sulfonic acid, and other buffers known in the art, e.g. those described by Good et al in *Biochem.*, 5, p. 467 (1966) and *Anal. Biochem.*, 104, 300 (1980).

The compositions of this invention are useful for analytical determination (i.e. quantitative, semi-quantitative or qualitative detection) of aqueous or non aqueous liquids, e.g. biological fluids, manufacturing processes, wastewater, food stuffs, etc. Determinations can be made of various analytes, including living cells (e.g. bacteria, yeast, fungi, etc.), enzymes (e.g. lipase, glucose oxidase, lactate oxidase, creatine kinase, α-glycerophosphate oxidase, lactate dehydrogenase, alanine aminotransferase, aspartate aminotransferase and other NADH-based or peroxidase-based assays which include dehydrogenase or reductase enzymes), biological or chemical reductants other than living cells which will reduce the ETA (e.g. ascorbate, cysteine, glutathione, etc.), metabolizable substances (e.g. glucose, lactic acid, triglycerides, cholesterol, etc.), immunoreactants (e.g. antigens, antibodies, haptens, etc.), and other determinations made via a single reaction or sequence of reactions which brings about reduction of the reducible compound and release of a detectable species.

The compositions of this invention are particularly useful in detecting or quantifying living sells in biological samples. Although any biological sample suspected of having living cells therein (e.g. food, tissue, ground water, cooling water, pharmaceutical products, sewage, etc.) can be analyzed for bacteria, yeast, fungi, etc. by this invention, the invention is particularly useful for bacterial detection in aqueous liquids, such as human and animal fluids (e.g. urine, cerebral spinal fluid, blood and the like as well as stool secretions) and suspensions of human or animal tissue. The practice of this invention is particularly important for detection of urinary tract infections in urine (diluted or undiluted).

The detection of living cells, and particularly of bacterial cells, is often carried out in the presence of a nutrient for those cells although its presence is not essential. Any nutrient media can be used which contains useful carbon, and optionally nitrogen, sources. Conventional nutrient mediums having proper components and pH are well known in the art. Particularly useful nutrients are readily metabolizable carbon sources, such as simple sugars (glucose, sucrose, raffinose, maltose, lactose, galactose, fructose, etc.), glycols (e.g. glycerol, sorbitol, etc.), carboxylic acids (e.g. acetic acid, lactic acid, citric acid, etc. or salts thereof) starch, tryptose and the like. Particularly useful nutrients are glucose or tryptose, alone or in combination.

The present invention is adaptable to either solution or dry element assays. For solution assay, an analytical composition containing a reducible compound which will provide a detectable species and an ETA can be prepared and mixed with a liquid test sample containing the living cells or analyte to be determined. The ETA can also be present in the test sample prior to mixing with the reducible compound. Generally the analytical composition is mixed with the test sample in a suitable container (e.g. test tube, petrie dish, beaker, cuvette, etc.). The resulting solution (or dispersion) is gently mixed and incubated for a relatively short time (i.e. up to about 30 minutes) at a temperature up to about 40° C., and generally from about 20° to about 40° C. The test sample is then evaluated by measuring the detectable species (e.g. chromogen or fluorogen) that has been released by reduction of the reducible compound. Such an evaluation can be done with suitable detection equipment.

The solution assay can also be carried out by contacting a porous, absorbent material, e.g. paper strip, containing the test sample with the analytical composition. The analyte in the test sample can migrate from the porous material into the composition thereby initiating the analytical reactions needed for the determination.

Generally, in a solution assay, the amount of reducible compound present is from about 0.01 to about 10 and preferably from about 0.05 to about 1, millimolar. The ETA is generally present in an amount of from about 0.01 to about 2 and preferably from about 0.05 to about 1, millimolar. Other reagents can be present in amounts readily determined by one skilled in the art.

Alternatively, this invention can be practiced in a "dry" assay which utilizes a dry analytical element. Such an element can be a simple absorbent carrier material, i.e. a thin sheet or strip of self-supporting absorbent or bibulous material, such as filter paper or strips, which contains the reducible compound and ETA or a dried residue of same. Such elements are known in the art as test strips, diagnostic elements, dip sticks, diagnostic agents and the like.

When employed in dry analytical elements, the reducible compound and ETA can be incorporated into a suitable absorbent carrier material by imbibition or impregnation, or can be coated on a suitable absorbent material. Useful carrier materials are insoluble and maintain their structural integrity when exposed to water or physiological fluids such as urine or serum. Useful carrier materials can be prepared from paper, porous particulate structures, cellulose, porous polymeric films, wood, glass fiber, woven and nonwoven fabrics (synthetic and non-synthetic) and the like. Useful materials and procedures for making such elements are well known in the art as exemplified by U.S. Pat. Nos. 3,092,465 (issued June 4, 1963 to Adams et al), 3,802,842 (issued Apr. 9, 1974 to Lange et al), 3,915,647 (issued Oct. 28, 1975 to Wright), 3,917,453 (issue Nov. 4, 1975 to Milligan et al), 3,936,357 (issued Feb. 3, 1976 to Milligan et al), 4,248,829 (issued Feb. 3, 1981 to Kitajima et al), 4,255,384 (issued Mar. 10, 1981 Kitajima et al), and 4,270,920 (issued June 2, 1981 to Kondo et al), and U.K. Pat. No. 2,052,057 (published Jan. 21, 1981).

A dry assay can be practiced to particular advantage with an analytical element comprising a support having thereon at least one porous spreading zone as the absorbent carrier material. The ETA and reducible compound can be in the spreading zone or in a different zone (e.g. reagent zone, registration zone, hydrophilic zone, etc.) or in separate zones. The spreading zone can be prepared from any suitable fibrous or non-fibrous material or mixtures of either or both. The void volume and average pore size of this zone can be varied depending upon the use intended. For example, if whole blood or other liquid samples containing cells or high molecular weight materials are to be assayed, the void volume and average pore size are generally greater than if serum or urine is to be assayed.

Useful spreading zones can be prepared using fibrous materials, either mixed with a suitable binder material or woven into a fabric, as described in U.S. Pat. No. 4,292,272 (issued Sept. 29, 1981 to Kitajima et al). Alternatively, and preferably, the spreading zone is prepared from polymeric compositions (e.g. blush polymers) or particulate materials, with or without binding adhesives, as described in U.S. Pat. Nos. 3,992,158 (issued Nov. 16, 1976 to Przybylowicz et al) and 4,258,001 (issued Mar. 24, 1981 to Pierce et al). Other useful spreading zone materials are described in W. German OLS 3,150,102 (published July 29, 1982) and Japanese Patent Publication 57(1982)-101760 (published June 24, 1982), both assigned to Konishiroku Photo. It is desired that the spreading zones be isotropically porous, meaning that the porosity is the same in each direction in the zone as created by interconnected spaces or pores between particles, fibers, polymeric strands, etc.

The dry analytical elements of this invention can be a single self-supporting porous spreading zone containing a reducible compound, an ETA and any other desired reagents for a particular use, but preferably such zone is carried on a suitable substrate (also known in the art as a support). Such a support can be any suitable dimensionally stable, and preferably, transparent (i.e. radiation transmissive) film or sheet material which transmits electromagnetic radiation of a wavelength between about 200 and about 900 nm. A support of choice for a particular element should be compatible with the intended mode of detection (reflection, fluorescence or transmission spectroscopy) and inert to chemical reagents and liquid samples used in the assay. Useful support materials include polystyrene, polyesters [e.g. poly(ethylene terephthalate)], polycarbonates, cellulose esters (e.g. cellulose acetate), etc.

The elements can have more than one zone, e.g. a reagent zone, a registration zone, radiation-blocking zone, subbing zone, etc. The zones are generally in fluid contact with each other, meaning that fluids, reagents and reaction products can pass between superposed regions of adjacent zones. Stated in another manner, fluid contact refers to the ability to transport components of a fluid between the zones in fluid contact. Preferably, the zones are separately coated layers, although two or more zones can be in a single layer, or a zone can contain two or more separate layers. Besides the Przybylowicz et al and Pierce et al patents noted above, suitable element formats and components are described, for example, in U.S. Pat. Nos. 4,042,335 (issued Aug. 16, 1977 to Clément) and 4,144,306 (noted above) and Reissue 30,267 (reissued May 6, 1980 to Bruschi).

In the elements of this invention, the amount of the reducible compound can be varied widely, but it is generally present in a coverage of up to about 1, and preferably from about 0.05 to about 0.2, $g/m^2$. The ETA is generally present in a coverage of up to about 10, and preferably from about 0.01 to about 1, $g/m^2$. Optional, but preferred reagents (e.g. nutrient, buffer, etc.) are generally present in the following coverages:

nutrient:
generally up to about 10, and preferably from about 0.1 to about 2, $g/m^2$ (used only in living cell detection), buffer (pH≦9):
generally up to about 5, and preferably from about 0.5 to about 2, $g/m^2$, and surfactant:
generally up to about 10, and preferably from about 0.2 to about 5, $g/m^2$.

One or more of the zones can contain a variety of other desirable, but optional, components, including activators, binders (generally hydrophilic), coupler solvents, etc. as is known in the art, as well as any reagents needed for assay of a particular analyte.

In one embodiment of this invention, an element for detection of microorganisms (e.g. yeast, fungi, bacteria, etc.) in an aqueous liquid comprises an absorbent spreading zone containing an ETA and a RIND compound, both of which are described above. It is desirable that these elements also contain a nutrient for the living cells and a buffer which maintains physiological pH under conditions of use (i.e. when contacted with a 1–100 μl sample of liquid). Such an element can be used to detect bacteria, for example, in a urine sample (pretreated to eliminate reductive interferents) by physically contacting the sample and element in a suitable manner, and detecting any moiety released from the RIND compound when it is reduced.

In another embodiment of this invention, an element for the determination of a nonliving biological or chemical analyte in an aqueous liquid comprises an interactive composition which is capable of providing a detectable species upon interaction with the analyte. This composition comprises a reducible compound (e.g. a RIND compound) which releases the detectable species when reduced, an ETA, and optionally, a nonionic surfactant and a buffer which maintains physiological pH during the assay, all of which are described above. Examples of such analytes are described above. The elements contain interactive compositions having suitable reagents which effect reduction of the ETA and reducible compound and release of a detectable species. The amount of detectable species detected can be correlated to the amount of analyte present in the liquid sample.

A variety of different elements, depending on the method of assay, can be prepared in accordance with the present invention. Elements can be configured in a variety of forms, including elongated tapes of any desired width, sheets, slides or chips.

The assay of this invention can be manual or automated. In general, in using the dry elements, an analyte or living cell determination is made by taking the element from a supply roll, chip packet or other source and physically contacting it with a sample (e.g. 1-100 $\mu$l) of the liquid to be tested. Such contact can be accomplished in any suitable manner, e.g. dipping or immersing the element into the sample or, preferably, by spotting the element by hand or machine with a drop of the sample with a suitable dispensing means.

After sample application, the element is exposed to any conditioning, such as incubation, heating or the like, that may be desirable to quicken or otherwise facilitate obtaining any test result.

Detection of an analyte or living cell is achieved when the reducible compound is reduced releasing a species which can be detected in a suitable manner. Preferably, as noted above, the detectable species is a colorimetric dye or fluorescent dye which can be detected with conventional colorimetric or fluorometric apparatus and detection procedures. If the detectable species is other than a chromogen or fluorogen, for example, a radioisotope, chemiluminescent or phosphorescent moiety, conventional radioisotopic, chemiluminescence or phosphorescence detecting means can be employed.

In the following preparations and examples, the reagents, materials and apparatus used were obtained as follows: Zonyl FSN TM surfactant from DuPont Co. (Wilmington, Del.), phenazine methosulfate and phenazine ethosulfate from Sigma Chemical Co. (St. Louis, Mo.), brain heart infusion (BHI) and tryptose nutrient media from Difco Labs (Detroit, Mich.), bacterial microorganisms from American Type Culture Collection (ATCC) in Rockville, Md. and Triton TM X-100 surfactant from Rohm & Haas (Philadelphia, Pa.). All other reagents were either obtained from Eastman Organic Chemicals (Rochester, N.Y.) or Aldrich Chemical Co. (Milwaukee, Wis.), or prepared using known starting materials and convention procedures.

For solution assays described below, emulsions of the RIND compounds were prepared by dissolving the RIND compound in N,N-dimethylformamide (DMF), adding surfactant, and then adding this solution to aqueous potassium phosphate (KP) buffer.

For examples 3-6, cells were grown in brain heart infusion medium at 37° C. and transferred daily. Cultures of Pseudomonas aeruginosa (ATCC 27853) were grown with shaking. All other organisms were grown in static culture. Forty ml of cells that were grown overnight were harvested, washed and resuspended in 10 ml of 0.05 molar KP buffer (pH 7.5). A stock solution was prepared with an approximate cell concentration of $3 \times 10^7$ cells/ml as determined by reading the optical density at 620 nm in a spectrophotometer. An optical density of 0.05 units corresponds to an approximate cell density of $3 \times 10^7$ cells/ml.

Measurement of dye release was determined in the following manner. The reaction mixture to be tested contained the following: the appropriate ETA solution (phenazine methosulfate, phenazine ethosulfate, 3 mg/ml in methanol, ETAs of this invention, 1.5 mg/ml in methanol), glucose and tryptose as cell nutrients, KP buffer (pH 7.5) and an aliquot of the microemulsion. After equilibration at 37° C., the reaction was initiated by the addition of an aliquot of the microorganism, typically 10-50 $\mu$l of a $10^8$ cells/ml suspension. Spectrophotometric absorbance was determined in a commercially available Perkin Elmer spectrophotometer at 636 nm. The results are usually expressed as net signal, i.e., the density produced by the sample minus the density for the control which contained all the reactants except the cells.

For examples 1, 2, 7 and 8, solution studies of ETA reactivity and background were carried out as follows:

E. coli cells (ATCC 25922) were grown in brain heart infusion (BHI) medium at 37° C. without shaking. Forty milliliters of cells that were grown overnight were harvested by centrifugation. The pellet was resuspended in 25 ml of buffer. An aliquot was diluted with the same buffer to obtain an optical density of 0.1 at 620 nm, as read by a commercially available Cary 219 spectrophotometer, and measured against a buffer blank. An optical density of 0.1 at 620 nm has been determined to correspond to a cell concentration of $6 \times 10^7$ cells/ml. A stock solution was prepared with a cell concentration of $6 \times 10^9$ cells/ml.

An aqueous composition of a RIND compound in DMF, surfactant and buffer (pH 7.5) was treated with 10% glucose solution and an aliquot of the cell stock solution. After equilibration at 37° C., the reaction was initiated by the addition of the appropirate ETA, dissolved in methanol. Reactions were followed by monitoring the appearance of dye at 636 nm using a Cary 219 spectrophotometer. For each ETA, experiments were performed on different days using freshly prepared cells. Multiple determinations of cellular dye release and background dye release (RIND compound and ETA) were obtained.

Reduction potentials (measured as the half-wave potentials $E_{\frac{1}{2}}$) were determined using the differential pulse polarographic technique. A commercially available PAR Model 174 polarographic analyzer was used. The solution medium was sodium phosphate buffer (pH 7.0, $\mu = 0.1$). Measurements were made against a standard calomel electrode. Values are reported versus the normal hydrogen electrode. The reduction potentials of the ETAs are listed in Table II.

The following preparations are representative of procedures to prepare ETAs useful in this invention. The intermediate and final compounds were characterized by mass spectral, nuclear magnetic resonance (NMR) and elemental analyses.

PREPARATION 1

Preparation of 2,3-Dimethyl-5-hydroxymethyl-1,4-benzoquinone (ETA I)

A mixture of 2,3-dimethylbenzoquinone (47.6 g, 0.35 mole) and 10% palladium on carbon catalyst in 100 ml tetrahydrofuran was shaken on a Paar apparatus under 40 psi (2.75 bars) of hydrogen for 1 hour at room temperature. The reaction mixture was filtered under a nitrogen atmosphere and the filtrate concentrated under vacuum to yield 39.9 g of 2,3-dimethyl-1,4-hydroquinone (intermediate A).

Methyl iodide (71.6 ml, 1.15 mole) was added to a stirring mixture of intermediate A (39.9 g, 0.288 mole), finely ground potassium carbonate (119.7 g, 0.866 mole) and dry acetone (230 ml). This mixture was refluxed for four days under a nitrogen atmosphere. The reaction mixture was filtered hot and the filtrate was concentrated to remove most of the acetone. The residue was added to 10% hydrochloric acid in ice water, and the precipitated solid was collected and dried. The yield was 45.2 g of 2,3-dimethyl-1,4-dimethoxybenzene (intermediate B).

Hydrogen chloride gas was bubbled into a stirred mixture of formaldehyde (24 ml, 37% in water), dioxane (48 ml) and concentrated hydrochloric acid (12 ml) for 15 minutes. The reaction was exothermic up to 75° C. When the temperature had dropped to 65° C., intermediate B (20 g, 0.12 mole) in 60 ml of dioxane was added dropwise to the mixture over 15 minutes. Hydrogen chloride gas was again bubbled into the reaction mixture for 10 minutes, after which the solution was stirred for 1 hour at room temperature. The solution was then poured into 1 liter of ice water, the precipitated material was collected and dried to yield 25.4 g of 5-chloromethyl-1,4-dimethoxy-2,3-dimethylbenzene (intermediate C).

A mixture of intermediate C (5 g, 0.023 mole) and anhydrous sodium acetate (7.1 g, 0.086 mole) in glacial acetic acid (35 ml) was refluxed for 20 hours. The reaction mixture was cooled to room temperature, diluted with 50 ml of water and extracted with dichloromethane. The organic extracts were washed with saturated sodium bicarbonate solution, dried, and concentrated to yield a dark syrup, which eventually crystallized to give 5.1 g of crude 5-acetoxymethyl-1,4-dimethoxy-2,3-dimethylbenzene (intermediate D).

A solution of intermediate D (5.1 g, 0.21 mole) in 100 ml of methanol and 25 ml of 10% sodium hydroxide was refluxed for one hour, then poured into ice water. The resulting solid was collected by filtration and dried to give 1.8 g of 1,4-dimethoxy-2,3-dimethyl-5-hydroxymethylbenzene (intermediate E).

To a mixture of intermediate E (1.8 g, 9 mmole), sodium acetate (7.5 g, 91 mmole), acetonitrile (134 ml) and water (29 ml), silver dipicolinate complex (19.2 g, 44 mmole, prepared by the method described by K. Kloc et al in Chem. Lett., 725. 1980) was added slowly with vigorous stirring over 30 minutes at room temperature. The mixture was stirred over 30 minutes longer, water (150 ml) was added, and the silver salts were filtered off and washed with chloroform. The filtrate was extracted several times with chloroform. The combined extracts were dried, concentrated to a small volume and chromatographed (silica, dichloromethane:ethyl acetate, 95:5). There was obtained 900 mg of ETA I, mp 71°-72° C. Calculated elemental analysis for $C_9H_{10}O_3$ is C, 65.1, H, 6.1, and O, 28.9. Elemental analysis found was C, 64.9, H, 5.9, and O, 28.7.

PREPARATION 2

Preparation of 5-Methylidane-4,7-dione (ETA XVII)

4,7-Dimethoxy-1-indanone, (intermediate A), prepared by the method of R. T. Coutts et al (Can. J. Chem., 52, 381 1974), was obtained as yellow needles from ethanol, mp 123°-126° C.

A mixture of intermediate A (19 g, 99 mmole), perchloric acid (2.5 ml of a 70% aqueous solution) and 10% palladium on carbon catalyst (2 g) in acetic acid (250 ml) was placed in a Paar bottle and shaken under 40 psi (2.75 bars) of hydrogen in a Paar shaker apparatus for 15 hours. Solid potassium acetate was added, and the mixture was filtered through a Celite pad. The Celite pad was washed with tetrahydrofuran, and the combined filtrates were poured into ice water (2 liters). The resulting white solid was isolated by filtration, washed with water, and dried under vacuum. Chromatography (silica, dichloromethane) afforded the desired product, 4,7-dimethoxyindane (intermediate B) as a white solid (8.5 g). White needles were obtained from ethanol:water (1:1), mp 82°-84°.

Hydrogen chloride gas was bubbled into a stirred mixture of formalin (2.2 ml, 37% in water), dioxane (4.4 ml) and concentrated hydrochloric acid (1.1 ml) for 15 minutes. The reaction was exothermic up to 75° C. When the temperature had dropped to 65° C., 4,7-dimethoxyindane (2.0 g, 11 mmole) in 10 ml of dioxane was added dropwise over 10 minutes. Hydrogen chloride gas was again bubbled into the reaction mixture for 10 minutes, after which the solution was stirred for one hour at room temperature. The reaction mixture was then poured into 600 ml ice water. The precipitated material was collected by filtration and dried to yield 2.3 g of 5-chloromethyl-4,7-dimethoxyindane (intermediate C).

A mixture of intermediate C (2.3 g, 10 mmole), ethanol (150 ml) and 10% palladium on carbon catalyst was added to a Paar bottle and shaken under 40 psi (2.75 bars) of hydrogen in a Paar shaker apparatus for 24 hours at room temperature. The reaction mixture was filtered through a Celite pad, washed with ethanol, and the filtrate concentrated to yield 2.1 g of 5-methyl-4,7-dimethoxyindane (intermediate D).

Cerric ammonium nitrate (18.1 g, 33 mmole) in acetonitrile (25 ml) and water (6 ml) was added dropwise to a stirred mixture of intermediate D (2.1 g, 11 mmole) in acetonitrile (25 ml). After one hour at room temperature, the reaction mixture was extracted with chloroform. The organic layer was dried and concentrated under reduced pressure to yield the crude product. This material was purified by column chromatography (silica, 95:5, dichloromethane:ethyl acetate) and rotary chromatography (silica, 80:20, dichloromethane:ligroin). There was obtained 570 mg of ETA XVII, mp 45°-47° C. Calculated elemental analysis for $C_{10}H_{10}O_2$ is C, 74.1, H, 6.2, and O, 19.7. Elemental analysis found was C, 73.7, H, 6.1, and O, 20.1.

PREPARATION 3

The Preparation of 6,7-Dimethoxy-1,2,3,4-tetrahydro-1,4-ethanonaphthalene-5,8-dione (ETA XXIII)

Intermediate A, 2,3-dimethoxybenzoquinone, was prepared by the procedure of J. C. Catlin et al (*J. Med. Chem.*, 14:45, 1971).

A mixture of intermediate A (1 g, 6 mmole), 1,3-cyclohexadiene (0.6 ml, 6 mmole), and toluene (15 ml) was refluxed about 15 hours under a nitrogen atmosphere. The solvent was removed under reduced pressure to yield 1.5 g of crude Diels-Alder adduct (intermediate B), which was used directly in the next step.

Intermediate B (1.5 g, 6 mmole) and potassium bicarbonate (1.23 g, 12 mmole) in 30 ml of dry methanol were refluxed under a nitrogen atmosphere for 30 minutes. The reaction mixture was filtered, and the filtrate was poured into dilute hydrochloric acid and ice water to precipitate the crude product. This crude material was dissolved in tetrahydrofuran (100 ml) and placed in a Paar bottle with 10% palladium on carbon catalyst, and shaken under 40 psi (2.75 bars) hydrogen in a Paar shaker apparatus for 2 hours. The reaction mixture was filtered, and the filtrate was concentrated under reduced pressure to yield 700 mg of a white solid, 6,7-dimethoxy-1,2,3,4-tetrahydro-1,4-ethano-5,8-dihydroxynaphthalene (intermediate C) which was used directly in the next step.

Intermediate C (700 mg) was dissolved in dichloromethane (70 ml) and lead peroxide (2 g) was added. After 3 hours at room temperature, the reaction mixture was filtered, and the filtrate was concentrated to a small volume and chromatographed (silica, dichloromethane:ethyl acetate, 95:5) to yield 600 mg of ETA XXIII, mp 104.5°-105.5° C. Calculated elemental analysis for $C_{14}H_{16}O_4$ is C, 67.7, H, 6.5, and O, 25.8. Elemental analysis found was C, 67.6, H, 6.2, and O, 25.6.

The following examples are provided to illustrate the practice of this invention.

EXAMPLE 1

Comparative Example Using RIND IX

This example compares the present invention using the ETAs described herein with embodiments of the Belly et al application U.S. Ser. No. 699,386 noted above using phenazine methosulfate (PMS) and phenazine ethosulfate (PES). The reducible compound used in this comparison is RIND IX of U.S. Ser. No. 699,386. RIND IX has the structure:

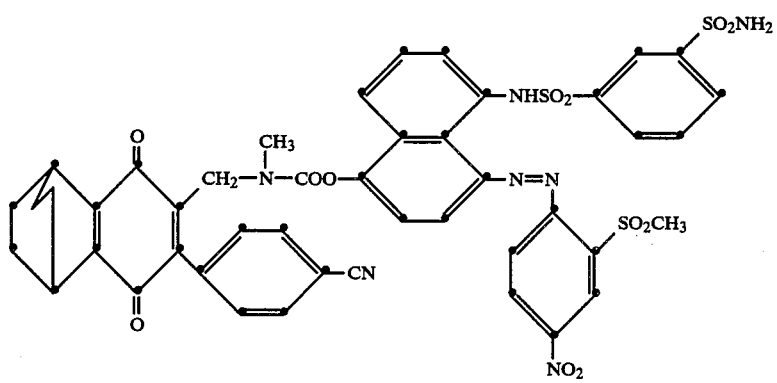

The following solutions were prepared:
(1) $9.8 \times 10^{-3}$ molar ETA in MeOH for each ETA,
(2) $1.7 \times 10^{-2}$ molar RIND IX compound in N,N-dimethylformamide (DMF),
(3) 50 μl of solution 2 + 100 μl of Triton TM X-100 + 5 ml of potassium phosphate (KP) buffer,
(4) 10% glucose solution, and
(5) $6 \times 10^9$ cells/ml in KP buffer.

Solutions 1, 3 and 5 were prepared daily. A 1 mm pathlength cuvette (400 μl capacity) was filled with 188 μl of solution 3, 188 μl of KP buffer, 6 μl of solution 4, and 12.5 μl of solution 5. The cuvette was covered with a rubber serum cap, to prevent evaporation, and thermally equilibrated to 37° C. Once equilibrated, the reaction was initiated by the addition of 3 μl of solution 1. Final solution concentrations of the initial reactants were: ETA ($7.7 \times 10^{-5}$ molar), RIND IX compound, ($7.6 \times 10^{-5}$ molar), *E. coli* cells ($6 \times 10^7$ cells/ml) and glucose ($8.8 \times 10^{-3}$ molar). Reactions were followed by monitoring the appearance of dye at 636 nm using a Cary 219 spectrophotometer.

For each ETA, three or four determinations were performed on different days. Multiple determinations of background dye release (RIND IX + ETA) were also obtained. Table II below lists data showing background and reduction potentials ($E_{\frac{1}{2}}$) of the ETAs. All of the ETAs of this example provided lower backgrounds than PMS after 10 minutes, and all but ETA XXVI provided lower background than PES after 10 minutes.

TABLE II

| ETA | % Background Release (10 Min) | % Background Release (30 Min) | $E_{\frac{1}{2}}$ (mV) |
|---|---|---|---|
| PMS | 1.7 | 3.5 | 96 |
| PES | 1.0 | 2.1 | 83 |
| I | 0.6 | 1.4 | 150 |
| II | 0.4 | 2.2 | 84 |
| III | 0.3 | 1.5 | 121 |
| IV | 0.6 | 1.4 | 154 |
| V | 0.3 | 1.5 | 102 |
| VI | 0.3 | 1.0 | 124 |
| VII | 0.4 | 1.8 | 50 |
| VIII | 0.1 | 0.6 | 60 |
| IX | 0.3 | 1.3 | 184 |
| X | 0.6 | 2.8 | 90 |
| XI | 0.3 | 1.1 | 126 |
| XVII | 0.3 | 0.8 | 176 |
| XXVI | 1.3 | 2.1 | 12 |
| XXVII | 0.7 | 1.6 | 22 |
| XXVIII | 0.2 | 0.8 | 122 |

EXAMPLE 2

Comparative Example Using RIND XX

Dye release from RIND XX (of Belly et al U.S. Ser. No. 699,386) was measured at 636 nm using the ETAs of the present invention and PMS under the same experimental conditions described in Example 1. RIND XX has the structure:

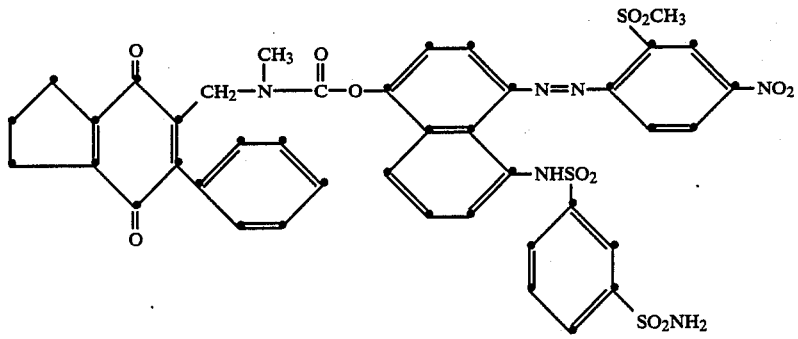

The results, listed in Table III below, indicate that all of the ETAs tested provided less background density than PMS, except ETA XXIX, which gives a slightly higher background after 10 minutes and about the same background after 30 minutes. Preferred ETAs I and III provided lower background and very fast dye release.

TABLE III

| ETA | Time (Min) for 100% Dye Release | % Background Release (10 Min) | % Background Release (30 Min) |
| --- | --- | --- | --- |
| PMS | 20 | 2.2 | 4.5 |
| I | 18 | 1.6 | 2.7 |
| III | 18 | 0.5 | 1.8 |
| XVII | 43 | 1.1 | 1.9 |
| XXVI | 25 | 1.5 | 3.1 |
| XXVII | 26 | 1.4 | 2.4 |
| XXVIII | 34 | 0.3 | 1.1 |
| XXIX | 29 | 3.2 | 4.6 |

EXAMPLE 3

Comparison of Response of ETAs in Determination of Pseudomonas aeruginosa

Test solutions were prepared with the following components: 1.5 ml of an aqueous composition of RIND IX, 25 μl of the appropriate ETA solution, 25 μl of glucose (5% solution) and 1.5 ml of potassium phosphate buffer (pH 7–7.5). After equilibration of the test solutions at 37° C., a 25 μl aliquot of an urinary tract infection (UTI) microorganism, *P. aeruginosa*, (about $1 \times 10^8$ cells/ml) was added, and the reaction was followed at 635 nm in a commercially available Perkin-Elmer Lambda 5 spectrophotometer. A Control solution without ETA was likewise monitored. Table IV below shows the absorbance change (ΔA) between sample and control after 15 and 30 minutes. The determinations using ETAs I and III show unexpectedly higher responses compared to those using phenazine methosulfate (PMS) and phenazine ethosulfate (PES).

TABLE IV

| | ΔA (15 min) | ΔA (30 min) |
| --- | --- | --- |
| ETA I | 0.683 | 1.921 |
| ETA III | 0.534 | 1.758 |
| PMS | 0.141 | 0.394 |
| PES | 0.088 | 0.237 |
| Control | 0.092 | 0.256 |

EXAMPLE 4

Response Using Tryptose as an Additional Nutrient with P. aeruginosa

Test solutions were prepared from the following components: 1.5 ml of an aqueous composition of RIND IX, 25 μl of the appropriate ETA solution, 25 μl of glucose (10% solution), 25 μl of tryptose (10% solution), and 1.5 ml of potassium phosphate buffer (pH 7.5). After equilibration of the test solution at 37° C., a 25 μl aliquot of *P. aeruginosa* (approx. $1 \times 10^8$ cells/ml) was added to each to give reaction mixtures, and the reaction was followed at 635 nm as in Example 3. Table V below shows the absorbance change (ΔA) after 15 and 30 minutes for two runs of the reaction mixtures. Both reaction mixtures 1 and 2 show improved dye release over all of the Control mixtures after both 15 and 30 minutes. The addition of tryptose as an additional nutrient gives a higher response.

TABLE V

| Rxn Mixture | ΔA 15 minutes | ΔA 30 minutes |
| --- | --- | --- |
| 1 | 1.076/1.061 | 4.008/3.987 |
| 2 | 0.570/0.430 | 1.849/1.561 |
| Control A | 0.134/0.135 | 0.393/0.412 |
| Control B | 0.030/0.031 | 0.074/0.089 |
| Control C | 0.061/0.058 | 0.161/0.170 |

Rxn Mixture 1 = *P. aeruginosa*, RIND IX, ETA III, glucose, tryptose
Rxn Mixture 2 = *P. aeruginosa*, RIND IX, ETA III, glucose
Control A = *P. aeruginosa*, RIND IX, PMS, glucose
Control B = ETA III, glucose, tryptose
Control C = PMS, glucose

EXAMPLE 5

Comparison of Response of ETAs in Determination of Several Organisms

Test solutions were prepared from the following components: 1.5 ml aqueous composition of RIND IX, ETA III and PMS (25 μl of the ETA solution), 25 μl of glucose (10% solution), 25 μl of tryptose (10% solution), and 1.5 ml of potassium phosphate buffer. After equilibration of the test solutions at 37° C., a 25 μl aliquot of the appropriate organism (approx. $1 \times 10^8$ cells/ml) was added and the reaction in each solution was followed at 635 nm as in Example 3. Table VI below shows the superior response of ETA III compared to phenazine methosulfate (PMS) with all of the listed organisms after 30 minutes. These results illustrate the improved sensitivity to most urinary tract infection microorganisms obtained with the present invention. It is also evident that the present invention shows an even response to most of the microorganisms. The only exception was the first S. pyogenes test which exhibited a low response with both ETAs tested because the microorganism was grown in BHI medium not supplemented with additional glucose. Excess glucose may be required for induction of metabolic enzymes.

TABLE VI

| Microorganism | ΔA 635 nm (30 minutes) | |
|---|---|---|
| | ETA III | PMS |
| Pseudomonas aeruginosa (ATCC 27853) | 3.602 | 0.226 |
| Escherchia coli (ATCC 25922) | 3.693 | 3.442 |
| Staphylococcus aureus (ATCC 25923) | 3.448 | 0.956 |
| Klebsiella pneumoniae (ATCC 13883) | 3.674 | 3.410 |
| Streptococcus pyogenes (ATCC 19615) | 0.208 | 0.121 |
| Streptococcus pyogenes* (ATCC 19615) | 2.968 | 0.121 |
| Streptococcus faecalis (ATCC 19433) | 3.478 | 3.312 |
| Proteus vulgaris (ATCC 13315) | 3.669 | 3.378 |

*This culture of S. pyogenes was grown in glucose buffer medium.

EXAMPLE 6

Determination of E. coli Using a Dry Analytical Element

A dry analytical element was prepared having the following format and components:

| | | |
|---|---|---|
| Spreading/ Reagent Layer | Poly(vinyltoluene-co-p-t-butyl-styrene-co-methacrylic acid) (61:37:2 weight ratio) beads (20–40 μm diameter) | 100–200 g/m² |
| | Poly(n-butyl acrylate-co-styrene-co-2-acrylamido-2-methylpropane sulfonic acid) (70:20:10 weight ratio) | 1–20 g/m² |
| | RIND IX from Table I of Belly et al, Serial No. | 0.05–1 g/m² |
| | D-glucose | 0.05–5 g/m² |
| | Triton ™ X-100 nonionic surfactant | 0.05–5 g/m² |
| | ETA III | 0.01–10 g/m² |
| | Poly(ethylene terephthalate) Support | |

A test solution was prepared with E. coli cells ($5 \times 10^8$ cells/ml) in sodium phosphate buffer (0.05 molar, pH 7.5). A Control solution contained only buffer. An aliquot (10 μl) of each solution was spotted on samples of the element. After 30 minutes of incubation at 37° C., the resulting reflection density ($D_R$) was measured in the element at 650 nm using a conventional spectrophotometer. This procedure was done six times and the $D_R$ results for each sample were averaged. The difference in $D_R$ between the test solution average and the Control solution average was 0.094 indicating that the E. coli cells initiated reduction of the RIND compound.

EXAMPLE 7

Determination of E. coli Using a Tetrazolium Salt as the Reducible Compound

In this comparative example, a tetrazolium salt (T-salt) having the following structure was used as the reducible compound:

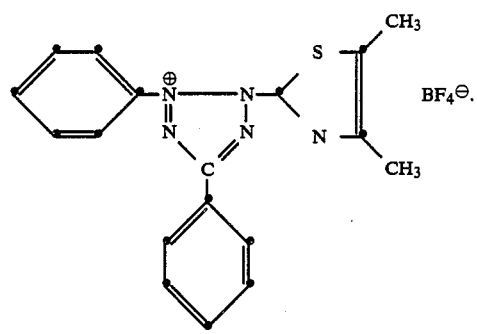

The determination of E. coli using several of the ETAs described herein was compared to a determination using phenazine methosulfate (PMS) as the ETA. The following solutions were used in the assay:

(1) potassium phosphate buffer (0.05 molar, pH 7.5),
(2) $9.8 \times 10^{-3}$ molar ETA in methanol,
(3) $1.2 \times 10^{-2}$ molar T-salt in phosphate buffer, and
(4) $6 \times 10^{-9}$ E. coli cells/ml in phosphate buffer, and
(5) 10% glucose.

A cuvette was filled with 3.1 μl of solution (2), 373 μl of solution (1), and 12.5 μl of solution (4), and 6.25 μl of solution (5), covered to prevent evaporation, and thermally equilibrated at 37° C. The oxidative-reductive reactions were then initiated by adding 3.3 μl of solution (3) to the cuvette. The reactions were followed by monitoring the appearance of formazon dye formed from the reduced T-salt at 550 nm using a commercially available Cary 219 spectrophotometer.

Table VII below lists the results of % dye formed in both 10 and 30 minutes as well as the background after those time periods. The assays of the present invention exhibited significantly less background compared to the assay using PMS while also showing generally better sensitivity (i.e. dye formed). The assay with ETA I showed faster dye formation after 10 minutes and reduced background after 30 minutes.

TABLE VII

| ETA | % Dye Formed (10 minutes) | % Background (10 minutes) | % Dye Formed (30 minutes) | % Background (30 minutes) |
|---|---|---|---|---|
| PMS | 30 | 1.5 | 64 | 4.1 |
| I | 39 | 0.6 | 55 | 1.2 |
| III | 36 | 0.1 | 72 | 1.4 |
| XXVII | 40 | 0.1 | 69 | 1.4 |

EXAMPLE 8

Determination of E. coli Using RIND XX

In this example, assays of this invention using several of the ETAs of Table I above were compared to an assay using PMS. The reducible compound was RIND XX of the Belly et al application, U.S. Ser. No. 699,386 noted above. The procedure followed was like that of Example 1. The release of dye was followed on a conventional spectrophotometer at 636 nm. Table VIII below lists the % dye released after 30 minutes as well as the % background at that time. All of the ETAs used generally promoted high dye release, but the assays of this invention had lower background.

TABLE VIII

| ETA | % Dye Release | % Background |
|---|---|---|
| PMS | 100 | 4.5 |
| I | 100 | 2.7 |
| II | 100 | 1.3 |
| III | 100 | 1.8 |
| IV | 96 | 1.8 |
| VIII | 96 | 1.1 |
| XVII | 96 | 1.9 |
| XXVI | 100 | 3.1 |
| XXVII | 100 | 2.4 |
| XXVIII | 96 | 1.1 |

The invention has been described in detail with particular reference to preferred embodiments thereof, but it will be understood that variations and modifications can be effected within the spirit and scope of the invention.

We claim:

1. A composition for the determination of an analyte in a liquid, said composition comprising:
   (a) an at least partially substituted benzo- or naphthoquinone electron transfer agent (ETA) which is capable of being reduced by said analyte and has an $E_{\frac{1}{2}}$ of from about $-320$ to about $+400$ mV as measured in an aqueous buffer solution at pH 7,
   (b) a reducible compound which provides a detectable species when reduced by said reduced ETA, and
   (c) a buffer which maintains the pH of said composition at pH 9 or less,
   said reducible compound being selected from the group consisting of
   tetrazolium salts
   dichloroindophenol dyes, and
   compounds of the structure $CAR\text{-}(R^1)_n$ wherein CAR— is an aromatic or quinone nucleus, $R^1$ is a moiety which comprises a shiftable detectable species, and n is 1 or 2, provided that said reducible compound is capable of being reduced at a pH of 9 or less to release said shiftable detectable species, and further provided that when $R^1$ is replaced with H, $CAR\text{-}(H)_n$ has an $E_{\frac{1}{2}}$ of either at least about $+100$ mV when measured in water, or of at least about $-650$ mV when measured in acetonitrile.

2. A composition for the determination of an analyte in a liquid, said composition comprising:
   (a) an at least partially substituted benzo- or naphthoquinone electron transfer agent (ETA) which is capable of being reduced by said analyte and has an $E_{178}$ of from about $-320$ mV to about $+400$ mV as measured in buffer at pH 7, and
   (b) a reducible compound represented by the structure
   $CAR\text{-}(R^1)_n$ wherein CAR— is an aromatic or quinone nucleus, $R^1$ is a moiety which comprises a shiftable detectable species, and n is 1 or 2,
   provided that said reducible compound is capable of being reduced at a pH of 9 or less to release said shiftable detectable species, and
   further provided that when $R^1$ is replaced with H, $CAR\text{-}(H)_n$ has an $E_{\frac{1}{2}}$ of either at least about $+100$ mV when measured in water, or of at least about $-650$ mV when measured in acetonitrile.

3. The composition of claim 2 wherein said reducible compound is a reducible intramolecular nucleophilic displacement (RIND) compound having the structure $CAR\text{—}R^1$ wherein CAR— is

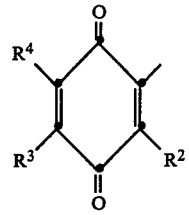

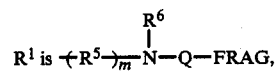

$R^2$ and $R^4$ are independently hydrogen, alkyl, aryl or an electron withdrawing group,
$R^3$ is $R^1$, hydrogen, alkyl, aryl or an electron withdrawing group, or $R^3$ and $R^4$, taken together, represent the atoms necessary to complete a fused carbocyclic ring,
$R^5$ is alkylene of 1 or 2 carbon atoms,
$R^6$ is alkyl, cycloalkyl or aryl,
Q is carbonyl or thiocarbonyl,
FRAG is a shiftable detectable species which provides a detectable species when released from said reducible compound, and
m is 0 or 1,
provided when $R^1$ is replaced with H, CAR—H has an $E_{\frac{1}{2}}$ of either at least about $+100$ mV when measured in water, or at least about $-650$ mV when measured in acetonitrile.

4. The composition of claim 2 wherein said ETA has the structure

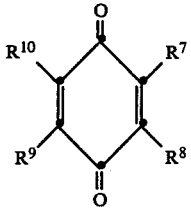

wherein $R^7$ and $R^8$ are independently hydrogen, alkyl, alkenyl, alkoxy, hydroxyalkyl, hydroxyalkoxy, alkoxyalkyl, alkoxyalkoxy, acetoxyalkyl, acetoxyalkoxy, aryl, alkaryl, a heterocycle or an heteroalkyl, and
$R^9$ and $R^{10}$ are independently selected from the substituents defined as $R^7$ or $R^8$, or taken together supply the atoms to complete a 4- to 8-membered fused carbocyclic or heterocyclic ring,
provided at least one of $R^7$, $R^8$, $R^9$ and $R^{10}$ is not hydrogen.

5. The composition of claim 4 wherein $R^7$ and $R^8$ are independently hydrogen, alkyl, alkoxy or hydroxyalkyl, and
$R^9$ and $R^{10}$ are independently selected from the substituents defined as $R^7$ or $R^8$, or taken together, supply the atoms to complete a 6- to 8-membered fused carbocyclic ring, and
said ETA has an $E_{\frac{1}{2}}$ of from about $-185$ mV to about $+400$ mV as measured in buffer at pH 7.

6. The composition of claim 2 wherein said ETA is 2,3,5-trimethyl-1,4-benzoquinone, 2,3-dimethyl-5- hydroxymethyl-1,4-benzoquinone or 2,3-dimethoxy-5-methyl-1,4-benzoquinone.

7. The composition of claim 3 wherein m is 1, at least two of $R^2$, $R^3$ and $R^4$ are independently electron withdrawing groups, or $R^3$ and $R^4$, taken together, represent the atoms necessary to complete a fused 5- to 7-membered carbocyclic ring, $R^5$ is methylene, $R^6$ is alkyl of 1 to 3 carbon atoms or phenyl, Q is carbonyl, and FRAG is a chromogen or fluorogen.

8. A dry analytical element for the determination of an analyte in a liquid, said element comprising an absorbent carrier material, an at least partially substituted benzo- or naphthoquinone electron transfer agent (ETA) which is capable of being reduced by said analyte and has an $E_{\frac{1}{2}}$ of from about $-320$ mV to about $+400$ mV as measured in buffer at pH 7, and a reducible compound which provides a detectable species when reduced by said reduced ETA.

9. The element of claim 8 wherein said ETA has the structure

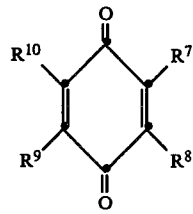

wherein $R^7$ and $R^8$ are independently hydrogen, alkyl, alkenyl, alkoxy, hydroxyalkyl, hydroxyalkoxy, alkoxyalkyl, alkoxyalkoy, acetoxyalkyl, acetoxyalkoxy, aryl, alkaryl, a heterocycle or an heteroalkyl, and $R^9$ and $R^{10}$ are independently selected from the substituents defined as $R^7$ or $R^8$, or taken together supply the atoms to complete a 4- to 8-membered fused carbocyclic or heterocyclic ring, provided at least one of $R^7$, $R^8$, $R^9$ and $R^{10}$ is not hydrogen, and said reducible compound is a reducible intramolecular nucleophilic displacement (RIND) compound having the structure CAR—$R^1$ wherein CAR— is

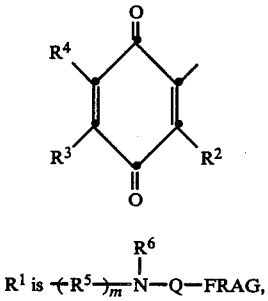

$R^1$ is $+R^5+_m N-Q-FRAG$, $R^2$ and $R^4$ are independently hydrogen, alkyl, aryl or an electron withdrawing group, $R^3$ is $R^1$, hydrogen, alkyl, aryl or an electron withdrawing group, or $R^3$ and $R^4$, taken together, represent the atoms necessary to complete a fused carbocyclic ring, $R^5$ is alkylene of 1 or 2 carbon atoms, $R^6$ is alkyl, cycloalkyl or aryl, Q is carbonyl or thiocarbonyl, FRAG is a shiftable detectable species which provides a detectable species when released from said reducible compound, and m is 0 or 1, provided when $R^1$ is replaced with H, CAR—H has an $E_{\frac{1}{2}}$ of either at least about $+100$ mV when measured in water, or at least about $-650$ mV when measured in acetonitrile.

10. The element of claim 9 wherein at least two of $R^2$, $R^3$ and $R^4$ are independently electron withdrawing groups, or $R^3$ and $R^4$, taken together, represent the atoms necessary to complete a fused 5- to 7-membered carboxylic ring, $R^5$ is methylene, $R^6$ is alkyl of 1 to 3 carbon atoms or phenyl, Q is carbonyl, FRAG is a chromogen or fluorogen, $R^7$ and $R^8$ are independently hydrogen, alkyl, alkoxy or hydroxyalkyl, and $R^9$ and $R^{10}$ are independently selected from the substituents defined as $R^7$ or $R^8$, or taken together, supply the atoms to complete a 6- to 8-membered fused carbocyclic ring, and said ETA has an $E_{\frac{1}{2}}$ of from about $-185$ mV to about $+400$ mV measured in buffer at pH 7.

11. The element of claim 8 comprising an interactive composition for said analyte.

12. The element of claim 8 comprising a carbon source nutrient for living organisms.

13. A method for the determination of an analyte in a liquid, said method comprising the steps of:

A. at a pH of 9 or less, physically contacting a sample of said liquid with an at least partially substituted benzo- or naphthoquinone electron transfer agent (ETA) which is capable of being reduced by said analyte and has an $E_{\frac{1}{2}}$ of from about $-320$ to about $+400$ mV as measured in an aqueous buffer solution at pH 7, and a reducible compound which provides a detectable species upon reduction by said reduced ETA, and B. detecting said detectable species, said reducible compound being selected from the group consisting of tetrazolium salts, dichloroindophenol dyes, and compounds of the structure CAR$+R^1)_n$ wherein CAR— is an aromatic or quinone nucleus, $R^1$ is a moiety which comprises a shiftable detectable species, and n is 1 or 2, provided that said reducible compound is capable of being reduced at a pH of 9 or less to release said shiftable detectable species, and further provided that when $R^1$ is replaced with H, CAR$+H)_n$ has an $E_{\frac{1}{2}}$ of either at least about $+100$ mV when measured in water, or of at least about $-650$ mV when measured in acetonitrile.

14. The method of claim 13 to determine a non-living analyte in the presence of an interactive composition for said analyte.

15. The method of claim 13 to determine bacterial cells.

16. The method of claim 13 wherein said reducible compound is represented by the structure CAR$+R^1)_n$ wherein CAR— is an aromatic or quinone nucleus, $R^1$ is a moiety which comprises a shiftable detectable species, and n is 1 or 2, provided that said reducible compound is capable of being reduced at a pH of 9 or less to release said shiftable detectable species, and further provided that when $R^1$ is replaced with H, $CAR{-}H)_n$ has an $E_{\frac{1}{2}}$ of either at least about $+100$ mV when measured in water, or of at least about $-650$ mV when measured in acetonitrile.

17. The method of claim 16 wherein said reducible compound is a reducible intramolecular nucleophilic displacement (RIND) compound having the structure $CAR{-}R^1$ wherein CAR is

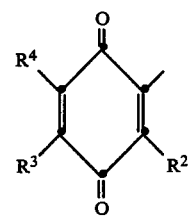

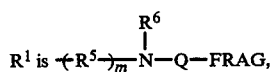

$R^2$ and $R^4$ are independently hydrogen, alkyl, aryl or an electron withdrawing group, $R^3$ is $R^1$, hydrogen, alkyl, aryl or an electron withdrawing group, or $R^3$ and $R^4$, taken together, represent the atoms necessary to complete a fused carbocyclic ring, $R^5$ is alkylene of 1 or 2 carbon atoms, $R^6$ is alkyl, cycloalkyl or aryl, Q is carbonyl or thiocarbonyl, FRAG is a shiftable detectable species which provides a detectable species when released from said reducible compound, and m is 0 or 1, provided when $R^1$ is replaced with H, $CAR{-}H$ has an $E_{\frac{1}{2}}$ of either at least about $+100$ mV when measured in water, or at least about $-650$ mV when measured in acetonitrile, and said ETA has the structure

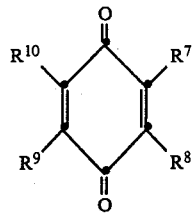

wherein $R^7$ and $R^8$ are independently hydrogen, alkyl, alkenyl, alkoxy, hyroxyalkyl, hydroxyalkoxy, alkoxyalkyl, alkoxyalkoxy, acetoxyalkyl, acetoxyalkoxy, aryl, alkaryl, a heterocycle or an heteroalkyl, and $R^9$ and $R^{10}$ are independently selected from the substituents defined as $R^7$ or $R^8$, or taken together supply the atoms to complete a 4- to 8-membered fused carbocyclic or heterocyclic ring, provided at least one of $R^7$, $R^8$, $R^9$ and $R^{10}$ is not hydrogen.

18. The method of claim 17 wherein $R^7$ and $R^8$ are independently hydrogen, alkyl, alkoxy or hydroxyalkyl, and $R^9$ and $R^{10}$ are independently selected from the substituents defined as $R^7$ or $R^8$, or taken together, supply the atoms to complete a 6- to 8-membered fused carbocyclic ring, provided said ETA has an $E_{\frac{1}{2}}$ of from about $-185$ mV to about $+400$ mV as measured in an aqueous buffer solution at pH 7.

19. The method of claim 13 wherein step B is carried out within 60 minutes of step A.

20. A composition for the determination of an analyte in a liquid, said composition comprising:
(a) an at least a partially substituted naphthoquinone electron transfer agent (ETA) which is capable of being reduced by said analyte and has an $E_{\frac{1}{2}}$ of from about $-320$ to about $+400$ mV as measured in an aqueous buffer solution at pH 7, said naphthoquinone being represented by the structure:

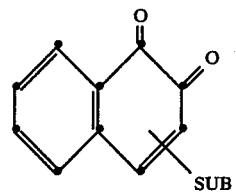

wherein SUB represents one or more electron withdrawing substituents, electron releasing substituents, or substituents which provide an aromatic or nonaromatic carbocyclic or heterocyclic ring fused with the naphthoquinone nucleus to provide said ETA with the desired $E_{\frac{1}{2}}$ value,
(b) a reducible compound which provides a detectable species when reduced by said reduced ETA, and
(c) a buffer which maintains the pH of said composition at pH 9 or less.

* * * * *